United States Patent
Lippert et al.

(10) Patent No.: US 8,060,196 B2
(45) Date of Patent: Nov. 15, 2011

(54) DEVICE FOR DETERMINING THORACIC IMPEDANCE

(75) Inventors: Michael Lippert, Ansbach (DE); Gerald Czygan, Buckenhof (DE)

(73) Assignee: Biotronik CRM Patent AG, Baar (CH)

( * ) Notice: Subject to any disclaimer, the term of this patent is extended or adjusted under 35 U.S.C. 154(b) by 955 days.

(21) Appl. No.: 11/293,398

(22) Filed: Dec. 2, 2005

(65) Prior Publication Data

US 2006/0135886 A1 Jun. 22, 2006

(30) Foreign Application Priority Data

Dec. 2, 2004 (DE) .................... 10 2004 059 082

(51) Int. Cl.
*A61B 5/05* (2006.01)
*G01R 27/00* (2006.01)
*G01R 27/02* (2006.01)

(52) U.S. Cl. ................ 600/547; 324/600; 324/603

(58) Field of Classification Search ........... 600/547; 324/600, 602, 603, 604, 606, 609
See application file for complete search history.

(56) References Cited

U.S. PATENT DOCUMENTS

| | | | |
|---|---|---|---|
| 5,522,860 A | 6/1996 | Molin et al. | |
| 5,752,976 A | 5/1998 | Duffin et al. | |
| 5,957,861 A | 9/1999 | Combs et al. | |
| 6,104,949 A | 8/2000 | Pitts Crick et al. | |
| 6,253,103 B1 * | 6/2001 | Baura ..................... | 600/547 |

(Continued)

FOREIGN PATENT DOCUMENTS

| | | |
|---|---|---|
| DE | 101 48 440 A1 | 4/2003 |
| EP | 0985429 | 3/2000 |

(Continued)

OTHER PUBLICATIONS

T. Palko, F. Bialokoz and J. Weglarz, "Multifrequency Device for Measurement of the Complex Electrical Bio-Impedance—Design and Application," Proceedings RC IEEE-EMBS & 14 BMESI— 1995, p. 1.45-1.46 (1995).

(Continued)

*Primary Examiner* — Max Hindenburg
*Assistant Examiner* — Adam Eiseman
(74) *Attorney, Agent, or Firm* — Hahn Loeser & Parks, LLP; John J. Cunniff

(57) ABSTRACT

An electromedical implant includes a measuring signal generator, an impedance measuring unit to determine the impedance of human or animal tissue, a control unit which, for controlling the measuring signal generator and the impedance measuring unit, is at least indirectly connected to the measuring signal generator and to the impedance measuring unit, as well as an electrode arrangement comprising at least two electrodes which can be directly or indirectly connected or at least temporarily connected to the measuring signal generator and to the impedance measuring unit, or to a connection for such an electrode arrangement. The measuring signal generator is designed to generate and emit a current pulse or a series of current pulses, and the control unit is designed at a specific point in time to cause the measuring signal generator (to generate and emit a current pulse, and to cause the impedance measuring unit to measure the voltage that is present between the electrodes connected to the measuring signal generator and the impedance measuring unit after the passing of at least two time periods of different length that start with commencement of the current pulse being emitted and end before the end of emitting the current pulse, and to issue a voltage value which in each case represents the measured voltage.

21 Claims, 5 Drawing Sheets

U.S. PATENT DOCUMENTS

| | | | |
|---|---|---|---|
| 6,360,123 B1* | 3/2002 | Kimchi et al. | 600/547 |
| 6,473,640 B1 | 10/2002 | Erlebacher | |
| 6,512,949 B1* | 1/2003 | Combs et al. | 600/547 |
| 6,553,262 B1 | 4/2003 | Lang et al. | |
| 2003/0004547 A1* | 1/2003 | Owen et al. | 607/5 |
| 2004/0102712 A1 | 5/2004 | Belalcazar et al. | |
| 2004/0147982 A1 | 7/2004 | Bardy | |
| 2004/0220632 A1* | 11/2004 | Burnes | 607/9 |

FOREIGN PATENT DOCUMENTS

| | | |
|---|---|---|
| EP | 1 238 630 A2 | 9/2002 |

OTHER PUBLICATIONS

E. Raaijmakers, J. Faes, H. Goovaerts, P. DeVries, R. Heethaar, "The Inaccuracy of Kubicek's One-Cylinder Model in Thoracic Impedance Cardiography," IEEE Transactions on Biomedical Engineering, vol. 44 (No. 1), p. 70-76, (Jan. 1997).

T. Palko, F. Bialokoz and J. Weglarz; Multifrequency Device for Measurement of the Complex Electrical Bio-impedance—Design and Application; Proceedings RC IEEE-EMBS & 14th BMESI; 1995; pp. 145-146; XP002489921.

* cited by examiner

DEVICE FOR DETERMINING THORACIC IMPEDANCE

BACKGROUND OF THE INVENTION

The invention relates to an electromedical implant, such as for example, a cardiac pacemaker, cardioverter, defibrillator or a pure monitoring implant, which comprises means to detect the impedance of human or animal tissue.

Furthermore, the invention relates to a system comprising at least one such electromedical implant which, in addition, comprises a wireless data interface, and to a patient device, a home monitoring service center or both.

From the state of the art, electromedical implants with means to determine the impedance of human or animal tissue are for example known from U.S. Pat. No. 5,957,861. There, a device is presented which by regular measuring and long-term monitoring of the impedance of pulmonary tissue facilitates early detection of the formation of pulmonary oedema. Oedema are accumulations of fluid, which occur in particular in patients with chronic cardiac insufficiency. The body reacts to the heart's reduced pumping capacity by means of compensation mechanisms which, however, in the long term result in progressive deterioration of the cardiac state. Among other things, the initial load is increased, and there is increased fluid retention. In an advanced stage, the increased pressure in the pulmonary circulation system can cause the formation of pulmonary oedema.

Impedance measuring of the pulmonary tissue utilizes the effect wherein body tissue containing fluid has a conductance which differs from that of healthy tissue. Experience shows that such impedance measuring makes possible earlier diagnosis of a pulmonary oedema than would be possible with conventional methods. The development of electromedical implants, which implants by way of impedance measuring provide such data to a physician which make it possible to diagnose a pulmonary oedema, is therefore attracting considerable attention. In this context, the integration of impedance measuring in a cardiac pacemaker has proven to be particularly advantageous.

Normally, cardiac pacemakers are implanted underneath the clavicle on the side opposite that of the heart, i.e. on the left side when viewed by the physician, and comprise an electrode which is anchored in the cardiac tissue of the patient. In this constellation, most of the patient's pulmonary tissue is located between the cardiac pacemaker housing and the electrode in the heart. If the cardiac electrode then injects a small current that is too weak to cause a heartbeat or some other reaction of the body, then at the same time the voltage that is present between the cardiac pacemaker housing and the electrode can be measured. When related to the value of the initiated current, this voltage is an indicator of the state of the pulmonary tissue of the patient. However, it is not sufficient to consider the absolute value of the measured impedance because the impedance to a large extent depends on the patient's anatomy and on the quality of the contact between the cardiac pacemaker electrode and the body tissue. Instead, the measured impedance values have to be stored for an extended period of time and must be compared with older values. If within days or weeks changes in the measured impedance value occur, this can indicate the formation of a pulmonary oedema.

Commercially available cardiac pacemakers and other electromedical implants usually feature a wireless data interface by way of which the cardiac pacemaker can transmit medical and technical data to an external device. If long-range telemetry has been integrated in the pacemaker, the impedance values of the pulmonary tissue, which impedance values have been determined by such a cardiac pacemaker, can be transmitted in this way to a home monitoring service center where the data is made available to an attendant physician for diagnosis. If on the basis of the transmitted data the attendant physician considers that there is a danger of a pulmonary oedema forming, the patient can be admitted for treatment long before physical discomfort occurs.

However, the device described in U.S. Pat. No. 5,957,861 is associated with a disadvantage in that long-term changes in the measured impedance values can also occur due to other causes, e.g. scarring (cicatrisation) of the tissue surrounding the cardiac pacemaker and the cardiac pacemaker electrode, or a change in the cardiac geometry due to advancing cardiac insufficiency.

SUMMARY

With a view to the state of the art, it is thus an aspect of the invention to present a device which makes it possible to more reliably determine pulmonary impedance irrespective of other long-term changes.

This aspect is met by the device according to the invention in that pulmonary impedance is measured such that in particular, the components of the impedance, which components are in particular caused by the pulmonary tissue, determine the value obtained.

The invention is based on the recognition that the capacitive component of the impedance to be determined, to a large extent, is due to the lung, while the ohmic components are determined by the totality of the body tissue. Accordingly, the invention is based on the idea that the device according to the invention is to separate the measured impedance value into its components so as to be able to exclude false alarms, or, even worse, any cover-up of the symptoms of an actually present oedema formation due to the above-mentioned or other effects.

If the body tissue situated between the cardiac pacemaker electrode and the cardiac pacemaker housing is converted to an electrical substitute connection diagram, then this results approximately in a series connection of an ohmic resistance which represents the contact resistance of the measuring electrodes and the cardiac tissue and other tissue, and a so-called resistance-capacitance element (RC element) which represents the pulmonary tissue.

Due to the novel measuring method of the present invention, the subject of the present invention is able to suppress impedance changes of tissue outside the lung (predominantly ohmic components) and is thus able to selectively isolate impedance changes in the lung by taking into account the capacitive component of the impedance.

For impedance measuring, the electromedical implant according to the invention in each case comprises a measuring signal generator, an impedance measuring unit, a control unit as well as at least two electrodes or a connection for electrodes, of which one can be the cardiac electrode used for cardiac stimulation, while the other can be the housing of the electromedical implant as a reference electrode. The electrodes or their connections are directly or indirectly connected or connectable to the measuring signal generator and to the impedance measuring unit. Both the measuring signal generator and the impedance measuring unit are again connected to the control unit.

Embodiments of the electromedical implant are also provided which comprise more than two electrodes, wherein these electrodes can be any electrodes known from the state of the art that are suitable for measuring. If more than two electrodes are provided, the electromedical implant can be designed to be operated with combinations of electrodes, which combinations are changeably specifiable during operation, so that the measuring signal generator and the impedance measuring unit can be connected to different electrodes.

In a first implementation of the teaching according to the invention, the measuring signal generator is designed to generate and emit a current pulse or a sequence of current pulses. Particularly preferably, biphasal current pulses are used as will be explained below. In this arrangement, the impedance measuring unit determines the impedance in that it determines half the voltage difference of the voltages measured during two antipolar current pulses. This is associated with an advantage in that as a result of this differential way of measuring, external interference voltages that are constant across the duration of measuring (electrochemical potential, IEGM) are suppressed. During emission of such a current pulse, the impedance measuring unit of the electromedical implant determines at least at two different points in time, the voltage that is present between the measuring electrodes, and thus emits a voltage value, which in each case represents the measured voltage, wherein said voltage value can also be a digitally encoded number.

The difference of the two voltages measured while a current pulse is emitted arises due to recharging the capacitive impedance components of the pulmonary tissue and provides an improved indicator of the condition of the patient. The ohmic resistances, which in the electrical substitute connection diagram of the body tissue are in series with the pulmonary tissue, are eliminated in a simple manner by calculating the difference of the two voltage values measured during the emission of a current pulse. In this way, the reading obtained is not falsified as a result of long-term changes to these ohmic resistances, for example, by scarring (cicatrisation) at the contact positions of the electromedical implant.

In an alternative implementation of the electromedical implant, the measuring signal generator is designed to generate current pulses of variable pulse duration. The control unit of the electromedical implant causes two current pulses, each of different duration, to be emitted, while at least one measuring procedure is carried out by the impedance measuring unit. In each instance, these measuring procedures take place after a fixed period of time from the point in time when the respective current pulse has ended. Due to the different duration of the current pulses, at the time of the two measuring procedures, a different period of time has elapsed since commencement of emission of the current pulse so that the capacitive elements of the pulmonary impedance were charged for different periods of time. The charge times of different duration result in different measuring voltages, whose difference again provides a better indicator of the present state of the pulmonary tissue than is the case with the pure impedance value itself.

In both alternative implementations of the scope and nature of the invention, more than two measuring procedures per measuring cycle can be carried out. In the first case, this takes place by means of more than two measuring procedures during emission of a single current pulse; in the second case, this takes place by emitting several current pulses of different duration and by carrying out one measuring procedure for each current pulse.

In an alternative implementation of the invention, the measuring signal generator is designed to generate sinusoidal currents of different frequencies.

Due to the different frequency behaviour of cardiac tissue and pulmonary tissue, two sinusoidal currents of the same amplitude but of different frequency, which sinusoidal currents are injected into the body tissue, generate sinusoidal voltages of different magnitude at the measuring electrodes. It is thus, for example, known that the specific resistance of pulmonary tissue for a frequency that is ten times higher drops to approximately 60% of the value at the lower frequency, whereas the specific resistance of cardiac tissue drops only by approximately 5%.

From the literature, the following values are known: p(10 kHz)/p(100 kHz) results in approximately 1.7 for pulmonary tissue, and approximately 1.05 for cardiac tissue, wherein p(f) denotes the specific resistance of the tissue at the frequency f.

This third implementation of the scope and nature of the invention is based on the teaching that from two impedance measurements at different frequencies, subtraction of the impedance value for the reading with a measuring signal of higher frequency from the impedance value of the reading with the low frequency results in a value obtained which is predominantly independent of the impedance of the cardiac tissue. For this reason, the object arising from the state of the art, namely to provide an improved indicator for the formation of pulmonary oedema, is also met by the third implementation method.

To provide an example of this: if by way of approximation, one assumes that the impedances of pulmonary tissue and cardiac tissue are connected in series, then the total impedance $Z_{total}$ for $Z_{total}=Z_{card}+Z_{pulm}$ DaZ(10 kHz)=p(10 kHz)/p(100 kHz)*Z(100 kHz) is as follows:

$$Z(10\ kHz)-Z(100\ kHz)=0.05*Z_{card}(100\ kHz)+0.7*Z_{pulm}(100\ kHz)$$

Consequently, if the impedances measured in relation to the two different frequencies are subtracted, the result to a large extent depends on the pulmonary impedance, and only to a small extent on the quality of the cardiac impedance that impairs the quality of the readings (ratio 14:1).

A further aspect of the invention relates to a system which, apart from an electromedical implant of the type shown, comprises a patient device or a home monitoring service center or both.

Modern electromedical implants, in particular cardiac pacemakers, defibrillators and the like, provide both the physician and the patient with a maximum of safety and convenience by means of their home monitoring functions.

In this arrangement, the implant keeps a record of information relating to diagnostics and therapy and transmits this information by way of a wireless data interface to an external patient device which the patient carries with him or her as directed by the physician. From there, the data is transmitted to the home monitoring service center, for example by way of a mobile telephony network, where said data is stored so as to be visually accessible by the physician. In this way, the physician can be directly informed about the progress of therapy and about the present state of health of patients, and is also able to react quickly to any changes in patient health. Among other advantages, indirect transmission of patient data by way of the patient device above all has an advantage in that the transmission results in the implant consuming considerably less energy; an important consideration since the batteries of said implant can only be changed in a surgical procedure.

Without home monitoring, the physician can only obtain this information within the framework of examining the patient. In critical situations, this would lead to undesirable delays in the flow of information. Furthermore, any examination involves a significant investment in time, both to the physician and to the patient. Frequent investigation impairs the patient's mobility and quality of life.

In the case of home monitoring, the implant information via the patient device is sent in the background (see also U.S. Pat. No. 6,553,262, U.S. Pat. No. 5,752,976) without this necessitating a change in the normal lifestyle of the patient. In other words, the patient enjoys the safety of being monitored by the physician without having to present him/herself for frequent examinations.

The claimed system comprising a novel electromedical implant and a patient device and/or a home monitoring service center expands the known advantages of such systems by the availability of improved measuring data which facilitate assessment of the state of health of a patient by his or her attendant physician.

In one particular embodiment of the electromedical implant, said implant comprises a control unit which is designed to determine the difference between the measured voltage values of two voltage readings taken at two different points in time. In this arrangement, these two voltage readings are taken at different points in time while a current pulse is emitted or while two different current pulses are emitted with different time spacing to the commencement of issuing the current pulses. The two voltage readings may be taken while two antipolar current pulses are emitted, wherein when the difference is formed, the signs of the measured voltages are taken into account. With the use of this biphasal voltage reading, external voltages (electrochemical potential, charge on the electrode, IEGM) are suppressed. By means of subtraction of the biphasal voltage readings, which were taken at different pulse durations, the temporally invariant component of the two measured voltages is eliminated from the result. This provides a particularly good indicator of the state of the pulmonary tissue.

In a particular embodiment of the invention, said invention is designed to take several readings while a single current pulse is emitted, or while several current pulses at different time spacing from commencement of emitting the respective pulse are emitted. In any real-life measuring arrangement, readings are always falsified by parasitic induction such as noise or electromagnetic interference fields. If more than two readings are carried out, the influence of these error sources can be reduced by mathematical compensating methods. With this procedure, the quality of the readings obtained is enhanced as the number of readings taken increases.

In the present case, essentially the capacitive component of the pulmonary impedance is determined, which is why the expected result has the characteristics of a charge- or discharge curve. In this embodiment, the control unit of the electromedical implant is therefore designed to calculate values of the compensating curve for each measuring point according to the known formula for charging a capacitor, wherein the values of the compensating curve depend in particular on the parameters $\tau$, the time constant, and $U_0$, the charge voltage. In this procedure, the control unit determines possible values of the compensating curve in relation to a multitude of parameter combinations or accesses such values stored in a table in a non-volatile memory before comparing these values with the actual values obtained. This comparison may be made by determining the minimum amount of the sum of the squares of the differences between values obtained and values of the compensating curve. The parameter combination, which in comparison to the actually determined value obtained, comprises the smallest sum of the squares of the individual deviations, is considered to be the result parameter combination.

If the electromedical implant is designed to emit several current pulses of different duration and to take only one voltage reading for each current pulse, the values determined for each current pulse are sorted according to the temporal spacing of the reading at the time of commencement of the respective current pulse, and are subsequently subjected to the same compensating method.

Since calculation of exponential functions can be very computation-intensive, as an alternative, a compensating curve of the values obtained can also be calculated by an approximation using a polynomial. In this case, the known method of the smallest error squares can be used, which method can be carried out with little computational effort in relation to polynomials.

In each case, the average person skilled in the art will recognise that a large range of mathematical error reduction methods are available which make it possible to calculate an improved overall result of readings on the basis of the original readings obtained.

Since the known exponential charge function rises steeply at first and then rises at a progressively flatter rate towards the end, readings in its initial region provide better information in relation to the actually existing parameters. For this reason, in an implementation of the invention, the invention is designed to take a greater number of voltage readings at commencement of issuing a current pulse than towards its end. In this way the reading error can mathematically be minimized so that the result parameters are particularly well suited to indicate changes in the state of the pulmonary tissue of the patient.

If the plurality of the values obtained is again determined while several current pulses are emitted, the measuring error of the result parameter combination can be reduced in an equivalent manner in that more current pulses of short pulse duration are emitted than are current pulses of longer duration.

In continuation of the scope and nature of the invention, the electromedical implant can further be designed, instead of or in addition to the result parameter combination, to calculate the difference between two values of the compensating curve that were determined according to the above-described method, and to issue this as the result. In this process, preferably the difference in the value of the compensating curve of the respective first and last voltage value determined during emission of a current pulse is determined.

In a respective implementation of the alternative measuring method, when several current pulses of different duration are emitted, the electromedical implant is designed to determine the difference of the values of the compensating curves relating to the voltage readings of the respective longest and shortest current pulse. Determining this voltage difference value from the value of the compensating curve provides an advantage in that an error-reduced value obtained in relation to the capacitive component of the tissue impedance is provided.

If the measuring signal generator of the electromedical implant is designed to generate current pulses, then a particularly preferred variant of the electromedical implant comprises a measuring signal generator which is designed to generate biphasal current pulses.

Biphasal current pulses comprise signal components of positive and negative displacement. At the zero passages, they can be divided into two or more sections which are associated with one of the two signs. For application in electromedical implants, in particular those biphasal current pulses are preferred in which the integrals of the positive and of the negative signal components resemble each other so that the difference between the two integrals is 0. Biphasal current pulses are preferred because they do not cause electrolysis effects and they do not influence the distribution of ions in body fluid and are therefore medically more compatible. Moreover, in this way "charging" of the electrode-tissue interface is avoided, and the sensing characteristics of the implant are not influenced. The influence which external voltages, in particular such direct voltage components that are not based on a voltage drop due to impedance, such as e.g. electrochemical potentials and the IEGM signals of the myocardium, have on the measuring signal can be eliminated by readings with biphasal pulses.

In the third implementation of the scope and nature of the invention, the measuring signal generator of the electromedical implant is designed to generate and emit sinusoidal currents of different frequencies. It is then the task of the impedance measuring unit to determine the amplitude of the sinusoidal voltage present at the measuring electrodes when a sinusoidal current is emitted, or to determine the phase difference between the sinusoidal measuring signal and the sinusoidal voltage present at the measuring electrodes. Both the ratio between amplitudes and the phase ratio between the measuring signal and the measured sinusoidal voltage can provide information about the capacitive component of the tissue impedance.

Amplitude readings are preferably taken by way of averaging the measuring voltage in a suitable filter or a phase-locked loop (PLL) and subsequent measurement of the resulting direct voltage; while the measuring of the phase ratio is carried out by detection of the zero passages of the measuring signal and the measured signal, and by determining the time periods between zero passages.

In one embodiment of the invention, said invention can be designed to gradually increase the frequency of the generated sinusoidal measuring signal until the impedance measuring unit detects a specific predefinable phase difference. To improve the reliability of readings, in a variation of the above, a period of time in which the predefinable phase difference is to be detected can be predefined. As an alternative, the impedance measuring unit can also be designed to detect maximum or minimum phase differences between the measuring signal and the measured signal during a predefinable period of time.

The quality of the reading can be improved in that the measuring voltage is first filtered in a suitable manner so that interference signals of other frequencies can be eliminated or suppressed. An embodiment of this alternative form of the electromedical implant therefore comprises a filter which is connected between the measuring electrode and the impedance measuring unit, and which is a low-pass or band-pass filter. The pass range of the filter is selected such that the frequency of the sinusoidal currents generated by the measuring signal generator is covered by it.

In one continuation of this embodiment of the electromedical implant, the pass range of the filter is smaller than the difference between the frequencies of the highest-frequency and the lowest-frequency sinusoidal current which is emitted by the measuring signal generator. So that the filter allows the respective measuring signals to pass, the pass range is in addition changeable so that during each individual reading any parasitic induction can be suppressed in a particularly broad band.

In a further embodiment, the electromedical implant comprises a subtracter which is designed to determine the difference of the amplitude voltages determined by the impedance measuring unit in relation to different sinusoidal currents, and to issue said difference as an amplitude differential value. In this way, the subtracter provides a result value which predominantly depends on the impedance of the pulmonary tissue and thus provides a particularly good indicator of the state of the pulmonary tissue.

According to the teaching which forms the basis of this alternative implementation of the invention, sinusoidal currents of a frequency between approximately 1 kHz and approximately 100 kHz are particularly preferred for determining the pulmonary impedance. Frequencies between 2 and 20 kHz can easily be controlled from a technical point of view, and the characteristics of body tissue are sufficiently well known if currents of these frequencies are injected.

Advantageously, an amplifier can be connected between the measuring electrode and the impedance measuring unit, which amplifier is designed to amplify or reduce the measuring voltage present between the measuring electrodes, and to feed the resulting voltage to the impedance measuring unit. By incorporating an amplifier with a changeable amplification factor, the electromedical implant can adjust the voltage present at the impedance measuring device such that as accurate a measurement as possible can be taken. In this variant of the electromedical implant, the value obtained of the impedance reading is related to the amplification factor of the amplifier. If the amplification factor of the amplifier in operation is adjustable such that the amount of the maximum value of the amplified voltage does not fall below a first voltage value and does not rise above a second voltage value, overloading the impedance measuring unit, which overloading would result in substantial measuring errors, can be prevented.

Since the voltage or amplitude to be determined by the impedance measuring unit normally comprises a time-variant or frequency-variant component, a further advantageous variant comprises a subtraction unit which is connected in series to the amplifier. This subtraction unit is designed, prior to the impedance measuring unit measuring the measuring voltage, to reduce said measuring voltage by a constant value that can be set so that if possible only the time-variant or frequency-variant component is fed to the impedance measuring unit. In this way, the measuring error during determination of the capacitive impedance component is minimized.

If the tissue impedance is only measured between two points in the body, the resulting value obtained acquires different tissue regions of different weighting, because the measuring current selects preferred paths through the tissue. If more than two electrodes are provided, the quality of the impedance readings can be improved in that the impedance between different combinations of electrodes is determined. In this arrangement, due to different positioning of the electrodes, the measuring current flows along different paths in the body. For this reason, several readings carried out in relation to different electrode arrangements can better take into account the totality of the pulmonary tissue. Therefore, in designs of the electromedical implant comprising more than two electrodes, embodiments in which the impedance measuring unit and the measuring signal generator can be connected with different electrodes are preferred.

Advantageously, the control unit of electromedical implants comprising more than two electrodes is designed to convert the values obtained that have been determined in relation to different electrode arrangements to an average value, which represents the different values obtained. If this average value is issued as a result, it makes possible a more compact representation and transmission as an improved indicator of the state of the pulmonary tissue of the patient.

Particularly preferably, all claimed embodiments of an electromedical implant with means to determine the impedance of body tissues are cardiac pacemakers, cardioverters or defibrillators. Typical positioning of such electromedical implants and their electrodes makes possible particularly easy integration of the means for determining the impedance of body tissue, which makes sense in particular in the case of patients suffering from cardiac insufficiency because these patients are exposed to a high degree to the danger of oedema formation.

Since, due to positioning of the cardiac electrode, measuring the tissue impedance also depends on the state of contraction of the heart, and on the content of blood in the blood vessels and capillaries, advantageously one embodiment of the electromedical implant provides for a cardiac activity detector which is designed to measure the cardiac cycle of a patient. In that the cardiac activity detector determines the cardiac cycle of a patient, the measuring signal generator can emit the current pulses at fixed points in time within a cardiac cycle so that identical or near-identical measuring conditions can be ensured in relation to readings at different points in time.

As an alternative, several readings are taken during one or several cardiac cycles, and the readings obtained are then averaged. In this way an impedance value can be obtained which is largely independent of the respective heart condition. Such averaging can also take place in the patient device or at the home monitoring service center.

The impedance of pulmonary tissue to a large degree depends on the air volume contained in the lungs, which is why one particular embodiment of the electromedical implant comprises a respiratory activity detector which is designed to measure the respiratory cycle of a patient. By means of the respiratory activity detector, the electromedical implant can take impedance readings at particular points in time within a respiratory cycle so that the points in time of several readings can, for example, be the moment of maximum exhaling, maximum inhaling, or some other point in time in the respiratory cycle. In this way the measured impedance values become largely independent of the respiratory state so that the comparability of values obtained at different points in time is improved.

Just as during averaging of the readings obtained from different impedance readings taken during one or several cardiac cycles, it is possible to obtain a comparison value that is independent of the cardiac state, a still further improved comparison value is obtained if averaging extends to readings obtained during an entire respiratory cycle or several respiratory cycles. A particular variant of the invention is thus designed to calculate an average value of the readings obtained during a multiple number of impedance readings taken during several respiratory cycles. Such averaging can also take place in the patient device or at the home monitoring service centre.

Instead of determining the average value, the median of the readings obtained in a series of impedance readings can be used. The median provides an advantage in that it can be determined with less computational effort and in that its value is not distorted by extreme values obtained which may be due to measuring errors.

All variants of the electromedical implant according to the invention may comprise a wireless data transmission interface which is designed to transmit not only other medical or technical data, but also the result values determined by the control unit, such as voltage difference value, average value, value of the first parameter $U_0$, value of the second parameter $\tau$ and amplitude differential value and/or one or several of the voltage values or amplitude values determined by the impedance measuring unit, by way of the wireless data transmission interface directly or indirectly by way of a patient device to a home monitoring service centre. All this data is preferably coded as binary digital characters. By way of wireless data transmission of patient data, the attendant physician can gain access to current values obtained that indicate the state of a patient's pulmonary tissue without said patient having to go to a hospital.

In a variant of the claimed system with an electromedical implant and a patient device and a home monitoring service center according to the invention, the patient device or the home monitoring service center are designed to calculate short-term and/or long-term average values of individual patient data received by the electromedical implant. These average values provide a good comparison value for assessing the last received patient data.

In a further variant, the patient device or the home monitoring service center are designed to compare received patient data with the calculated short-term and long-term average values, for example by subtracting the average values from the patient data.

A variant of the system makes it possible for the attendant physician to conveniently look after a multitude of patients in that the system is designed to indicate any deviations in the patient data compared to average values. In this way, particularly pronounced deviations can be highlighted separately.

Below, the invention is described with reference to diagrams of embodiments and further explanatory diagrams.

DETAILED DESCRIPTION OF THE INVENTION

Figure 1:
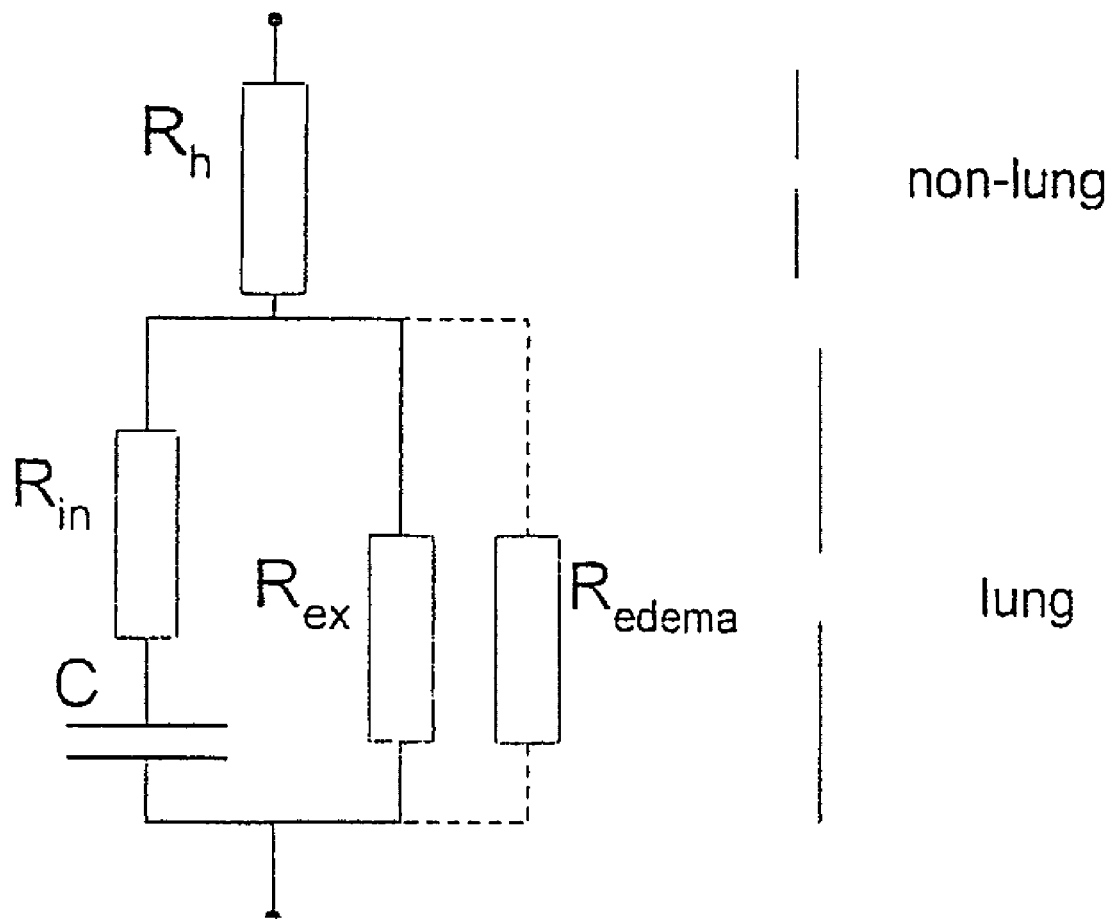
FIG. 1 diagrammatically shows an electrical substitute connection diagram of the body tissue between the two measuring electrodes in their operative states.

FIG. 1 shows a network of several discrete elements. This essentially results in a series connection of an ohmic resistance $R_h$, and in a parallel connection of several resistances and a capacitance C, where $R_h$ denotes the resistance of the cardiac tissue in which a measuring electrode is arranged. For the sake of simplicity, other contact resistances of the two measuring electrodes are included in the resistance $R_h$. Parallel connection of the capacitance C and the ohmic resistances $R_{in}$, $R_{ex}$ and $R_{oedema}$ in approximation describes the resistance behaviour of the pulmonary tissue $R_{in}$, $R_{ex}$ and C which is situated between the heart and the electromedical implant. $R_{in}$, $R_{ex}$ and C characterize the electrical behavior of the healthy pulmonary tissue, while $R_{oedema}$ only occurs if the ohmic resistance of the pulmonary tissue is reduced due to oedema formation. In the substitute electrical replacement diagram, the ohmic resistance reduced by the oedema is taken into account by parallel connection of the resistance $R_{oedema}$.

While the time-invariant part of the measuring voltage generated by injecting a current pulse depends on the series connection of the resistance $R_h$ and the resistances $R_{in}$, $R_{ex}$ and $R_{oedema}$, the time-variant part of the measuring voltage is solely determined by the resistances $R_{in}$, $R_{ex}$, $R_{oedema}$ and by the capacitance C. The dependence of the time-variant voltage component on $R_{oedema}$ is considerably stronger than that of the time-invariant component. This shows how the meaningfulness of the impedance values obtained increases by determining the time-variant measuring voltage component, and in addition how changes in the resistance $R_{in}$ as a result of cicatrisation of the tissue surrounding the measuring electrodes can be eliminated as a source of errors in long-term observation of the development of the tissue impedance values.

Figure 2:
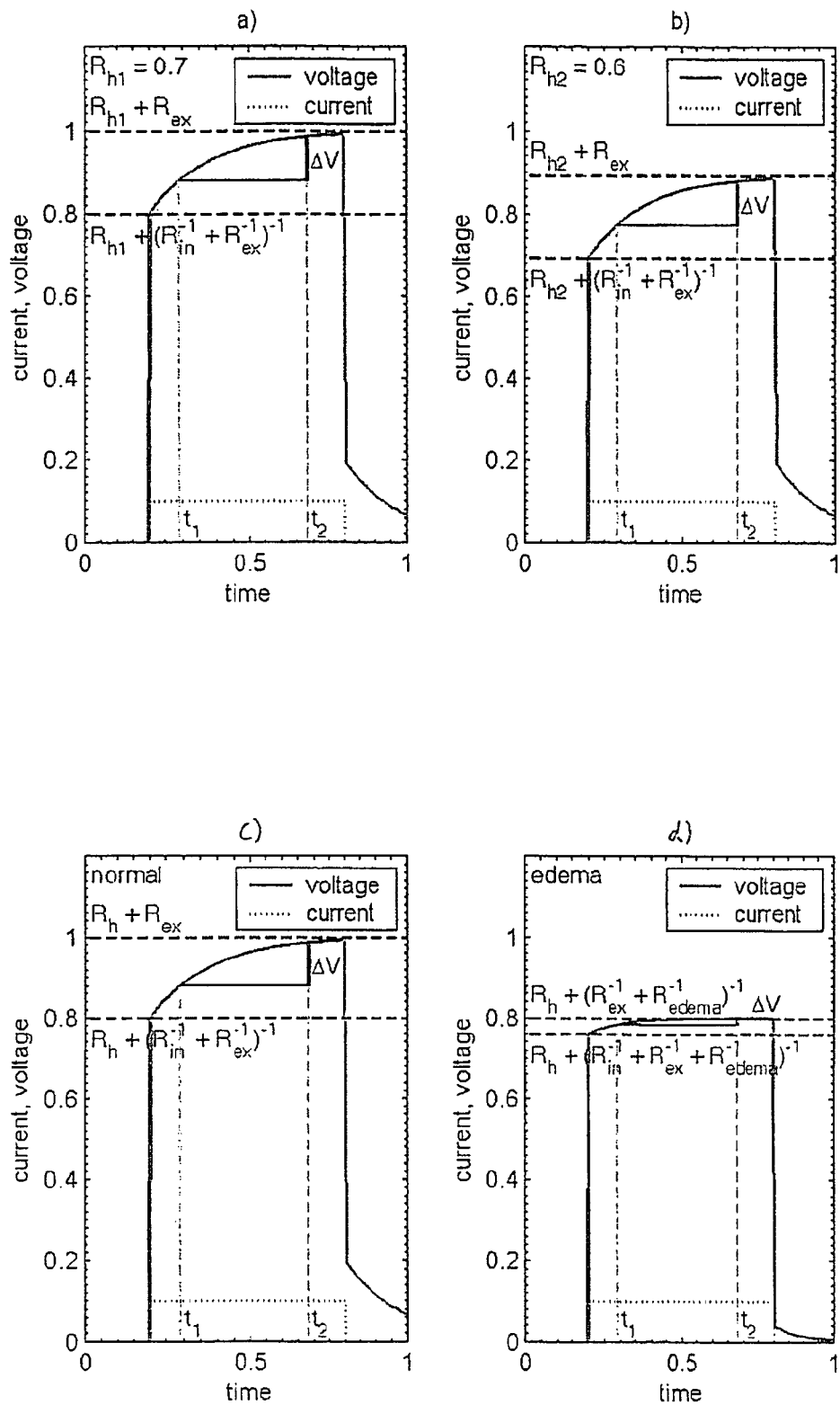
FIG. 2 shows four sub-images a, b, c and d, depicting different voltage gradients as they can occur during injection of a biphasal current pulse into the body tissue.

FIG. 2 is divided into two sub-images, each in turn again being split into two partial images. This results in a total of four partial images denoted a to d. The first sub-image in the partial images a and b shows two voltage curves as they might result if a square current pulse is injected into the body tissue. The two voltage curves were calculated in relation to substitute connection diagrams of the body tissue that were identical except for the value of the resistance $R_h$. In sub-image b, the value of the resistance $R_h$ was reduced, which results in a decrease of the maximum value of the voltage curve. A comparison of the two partial images a and b clearly shows that the reduction in resistance merely results in a reduction of the constant base part of the voltage curve, while the curve of the time-variant top part remains the same. This behaviour confirms that the difference between two measured voltage values obtained at different points in time $t_1$ and $t_2$ provides an indicator which is independent of the resistance of the cardiac tissue $R_h$.

In the second sub-image of FIG. 2, at constant resistance $R_h$, a resistance $R_{oedema}$ was incorporated in the substitute connection diagram. This resistance, which is connected in parallel to the resistance $R_{ex}$, reduces the resistance situated parallel to the capacitance C so that this capacitance can be charged or discharged more quickly. While a comparison of the two voltage curves in partial images c and d clearly shows a decrease in the amplitude of the time-variant component of the voltage curve, the constant part of the voltage signals remains almost constant, despite the resistance $R_{oedema}$ being added. It can therefore be concluded that the difference between the two values obtained at the beginning and at the end of emission of the current pulse provides an indicator which is essentially independent of the resistance of the cardiac tissue but is highly dependent on the formation of oedema.

Figure 3:
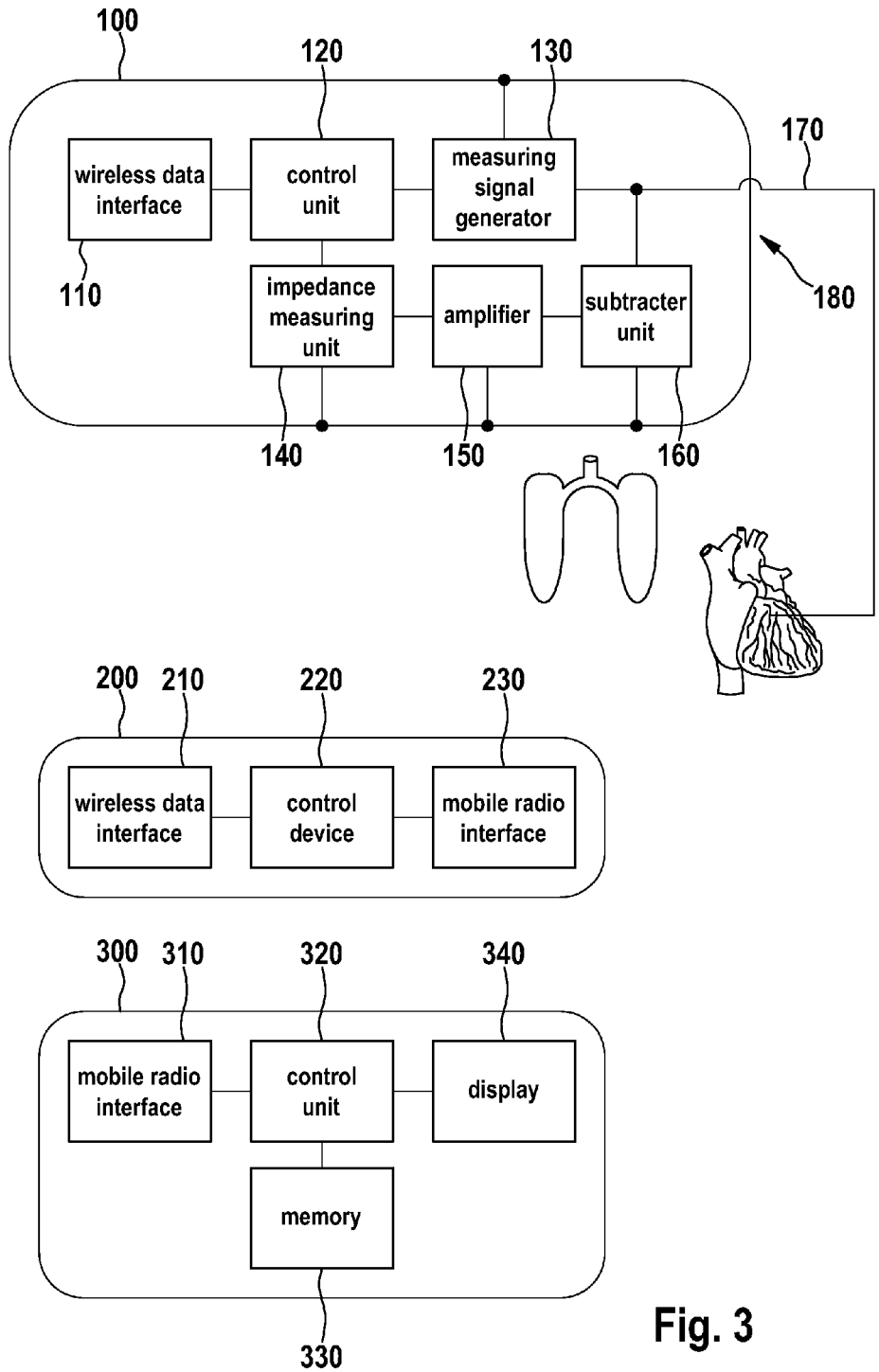
FIG. 3 shows a block diagram of an embodiment of the invention.

The system shown in FIG. 3, comprising a cardiac pacemaker 100, a patient device 200 and a home monitoring service centre 300 serves as an example of a system of the type claimed.

For communication with the patient device 200, the cardiac pacemaker 100 comprises a wireless data interface 110 which is connected to the central control unit 120 of the cardiac pacemaker 100. The control unit 120 is connected to the measuring signal generator 130 and to the impedance measuring unit 140 and controls said impedance measuring unit 140 for the purpose of determining the impedance of the pulmonary tissue. It is the task of the measuring signal generator 130 to generate measuring signals and to emit them by way of the connected cardiac electrode 170. The housing of the cardiac pacemaker 100 serves as a reference electrode. The subtracter unit 160 is connected between the housing and the cardiac pacemaker electrode 170, wherein said subtracter unit 160 is designed to deduct a constant offset voltage from a measuring voltage applied to the two electrodes, and to feed the resulting voltage to the amplifier 150. The amplifier 150 amplifies the measuring voltage received by the subtracter unit 160 so that the measuring range of the impedance measuring unit 140 is used to the fullest possible extent without overloading the impedance measuring unit 140. At points in time that are determined by the control unit 120, the impedance measuring unit 140 determines the measuring voltage present at its measuring input, and provides a corresponding measured voltage value to the control unit 120. In this arrangement, the control unit 120 is designed to store the measured voltage values received by the impedance measuring unit 140 and to calculate at least the difference between two subsequent impedance readings. If more than two readings are taken for each current pulse emitted, or if several current pulses of different duration are emitted, during which an impedance reading is taken, the control unit 120 is designed to calculate compensating curve values so that an error-reduced result value can be provided. The control unit 120 sends this result value and if need be, further measuring data, by way of the wireless data interface 110 to the patient device 200.

The patient unit 200 comprises a wireless data interface 210, a control device 220 and a mobile radio interface 230. Instead of the mobile radio interface it is also possible to provide an interface for a wire-bound form of communication, for example by way of an ordinary telephone line. The wireless data interface 210 receives the patient data sent by the wireless data interface 110 of the cardiac pacemaker 100 and conveys this patient data to the control unit 220 of the patient device 200. The control unit 220 forwards the received patient data either unchanged by way of the mobile radio interface 230 to the home monitoring service centre 300, or it relieves said mobile radio interface 230 in that it applies tasks which would otherwise have to be performed by the control unit 320 of the home monitoring service centre to the patient data prior to transmitting said patient data to the home monitoring service centre 300.

The home monitoring service centre 300 receives the patient data sent by the patient device 200 by way of a mobile radio network, by way of the mobile radio interface 310 which is connected to the control unit 320 of the home monitoring service centre 300. If the patient device instead of a mobile radio interface 230 comprises an interface for wire-bound communication, instead of, or in addition to, the mobile radio interface 310, a wire-bound data transmission interface is provided for the home monitoring service center. In the example shown, the home monitoring service centre 300 additionally comprises a memory 330 as well as a display 340. The control unit 320 is designed to store the received patient data in the memory 320, and to calculate short-term and long-term average values of the patient data received at the time and previously. Furthermore, the control unit 320 compares the received patient data with the previously calculated short-term average values and long-term average values of the patient data. If in this process, the control unit 320 detects a discrepancy between the values obtained at the time and the average values, if applicable beyond a selectable extent, then the control unit 320 displays this discrepancy on the display 340, using suitable visual or acoustic means.

Figure 4:
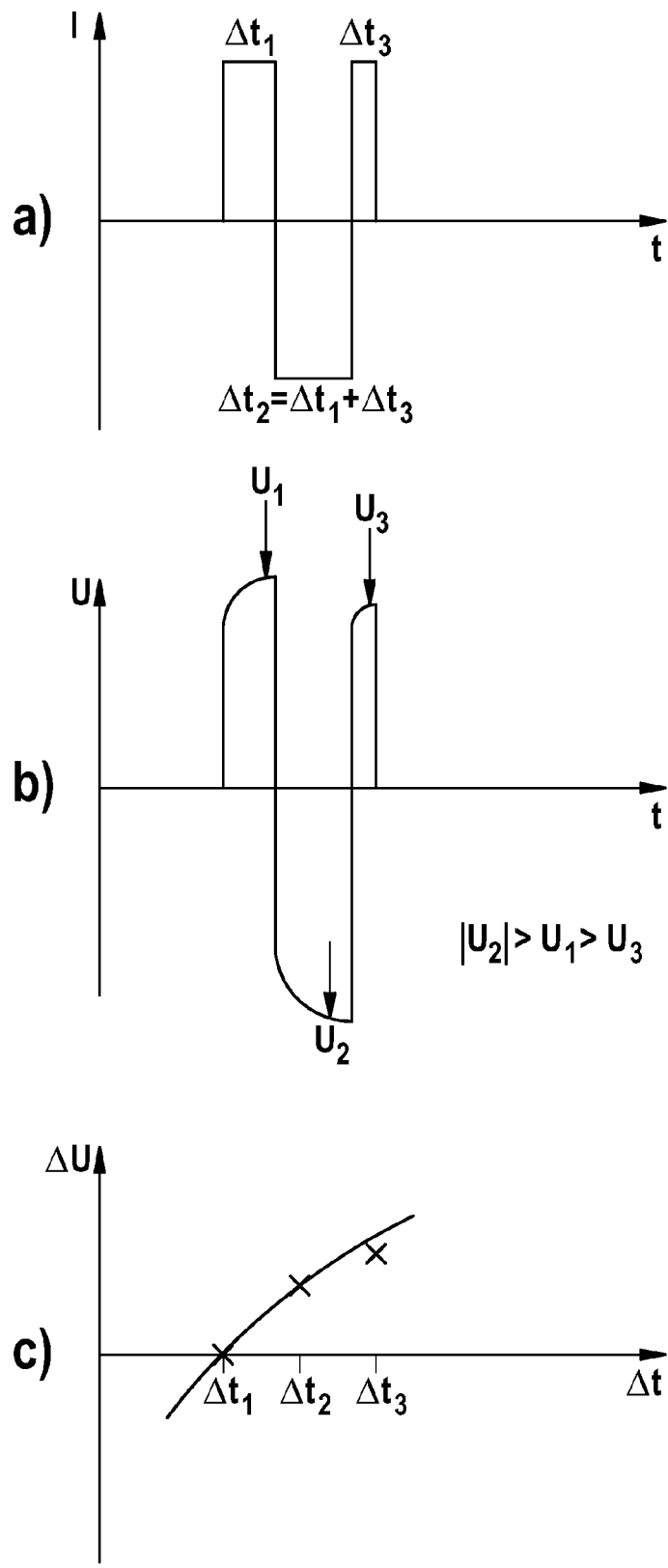
FIG. 4 shows three coordinate systems that show possible current gradients and voltage gradients during implementation of the measuring method.

FIG. 4 shows three coordinate systems which represent possible gradients of an impedance measuring procedure. The first of the coordinate systems shows a biphasal current pulse which can be divided into three sections: two positive sections and a negative section situated between said positive sections. The pulse duration of the three sections is selected such that the times $\Delta t_1$ and $\Delta t_3$ precisely add up to the pulse duration $\Delta t_2$ of the negative pulse. This ensures that the integrals of the positive and negative signal components cancel each other out, which ensures better medical compatibility.

The second coordinate system shows a qualitative gradient of a measuring voltage as it could result during injection of the biphasal current pulse shown in the first coordinate system. During emission of the current pulse, a total of three voltage readings are taken; one reading during each segment of the biphasal current pulse. All three voltage readings are taken at a constant temporal space to the end of the respective segment of the current pulse, so that in relation to the three segments, three segments of different spacing to the beginning of the respective segment result. Due to the different charging durations of the electrical capacity C of the lungs, all three voltage readings return different values obtained. The amount of the value obtained of the negative segment of the biphasal current pulse is largest due to the longest charge duration; that of the first segment of the current pulse is second largest; while that of the third segment is smallest.

In the third coordinate system shown in FIG. 4, the values $U_3$ obtained which relate to the shortest segment of the biphasal current pulse are superimposed as voltage differences on the temporal spacings $\Delta t$ of each voltage reading from the time of issue of the corresponding segment of the biphasal current pulse. Due to this subtraction, the resulting voltage difference $\Delta U_3$ relating to the shortest segment of the current pulse in the coordinate system is 0. Apart from the three voltage differences, a compensating curve has been entered in the coordinate system, which compensating curve follows the known charge characteristics of a capacitor. The parameters $\tau$ and $U_0$, which determine the gradient of this compensating curve, can serve as a resulting value of pulmonary impedance measuring. As an alternative, or in addition, the difference between the compensating curve values relating to the second and third reading can be determined.

Figure 5:
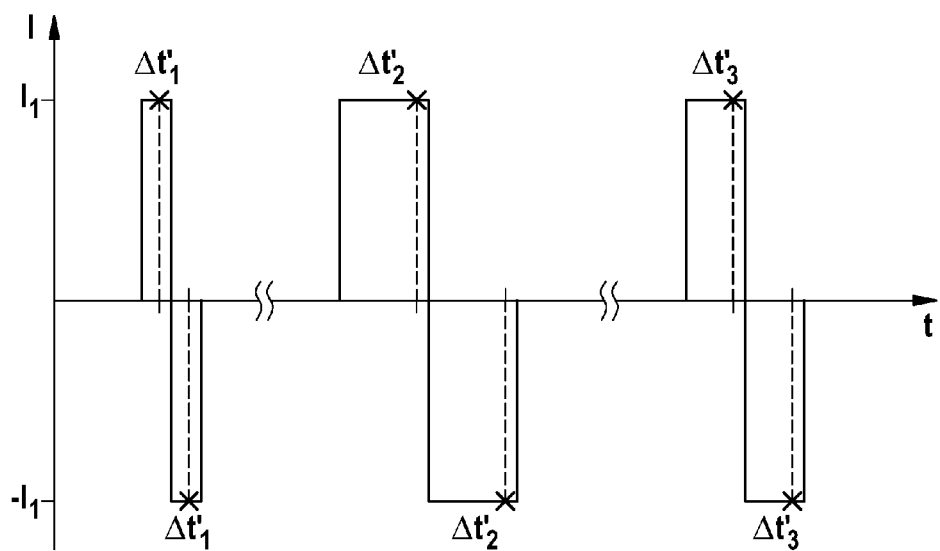
FIG. 5 shows a further example of a sequence of biphasal current pulses as they are advantageously used for differential measuring of the tissue impedance.

FIG. 5 shows a further temporal gradient of a sequence of current pulses for determining the impedance of the tissue situated between the electrodes. The points in time when impedance readings were taken are marked on the ordinate.

Readings are taken differentially, i.e. biphasal current pulses are used which comprise two directly consecutive current pulses that are of the same duration but are antipolar. During each of the two halves of the current pulse, a reading is taken at the same temporal spacing to the beginning of emission of the respective current pulse half. The amounts of the voltages determined during the two partial readings are added, and the intermediate result is halved. In this way, parasitic direct voltages that might falsify the readings are eliminated.

The sequence of biphasal current pulses shown depicts several current pulses of different widths. In this arrangement, for each biphasal current pulse only one differential impedance reading comprising two partial readings is taken. In order to determine the capacitive component of the impedance, the readings obtained in relation to current pulses of different width or different length since the beginning of emission of the corresponding current pulse are evaluated as already described. As an alternative, several readings can also be taken for each current pulse half. In this case the individual readings must be allocated according to their temporal space at the beginning of the respective current pulse half to the corresponding readings of the other current pulse half, before the average is taken so as to eliminate interfering direct voltages and before the capacitive component of the tissue impedance is determined.

The invention claimed is:

1. An electromedical implant comprising at least a measuring signal generator;
   an impedance measuring unit to determine the impedance of human or animal tissue;
   a control unit which, for controlling the measuring signal generator and the impedance measuring unit, is at least indirectly connected to the measuring signal generator and the impedance measuring unit;
   as well as an electrode arrangement comprising at least two electrodes which can be directly or indirectly connected or at least temporarily connected to the measuring signal generator and to the impedance measuring unit, or to a connection for such an electrode arrangement;
   wherein:
   the measuring signal generator is designed to generate and emit first and second current pulses of variable pulse duration;
   and wherein the control unit is programmed at least at first and second different points in time to cause the measuring signal generator to generate and emit the first current pulse and the second current pulse, so that emission of the first current pulse is finished before emission of the second current pulse starts, and the pulse duration of the emitted first and second current pulses are different;
   and to cause the impedance measuring unit to measure the voltage that is present between the electrodes connected to the measuring signal generator and the impedance measuring unit
   by measuring a first voltage at the beginning of a specific period of time that ends when emitting the first current pulse ends, and to issue the first voltage as a voltage value which represents the measured first voltage; and
   by measuring a second voltage at the beginning of said specific period of time that ends when emitting the second current pulse ends, and to issue the second voltage as a voltage value which represents the measured second voltage.

2. The electromedical implant according to claim 1, wherein the control unit is programmed to determine a value which represents a difference between the first and second voltage values measured by the impedance measuring unit during the first and second current pulses of different duration emitted by the measuring signal generator and to issue this difference as a voltage difference value.

3. The electromedical implant according to claim 2, wherein:
   the control unit is programmed to cause the measuring signal generator to generate and emit a current pulse at more than two different points in time so that emission of an earlier current pulse ends before emission of an immediately subsequent current pulse starts, and the pulse durations of the emitted earlier and immediately subsequent current pulses differ from each other;
   and to cause the impedance measuring unit to measure the voltage that is present between the electrodes that are connected to the measuring signal generator and to the impedance measuring unit by measuring a pulse voltage at the beginning of a specific period of time that ends when emission of the respective current pulse ends; and
   and wherein furthermore, the control unit is programmed, for each of the points in time of causing a voltage reading to be taken depending on a first parameter $U_0$ and/or a second parameter $\tau$, to determine a multitude of compensating-curve values $U_A$ which are calculated according to the formula $$U_A = U_0 * (1 - e^{-t/\tau})$$

wherein e denotes Euler's integral and t denotes the duration between the point in time of commencement of emission of the current pulse, during which emission the control unit has caused the voltage reading, in relation to which the multitude of compensating-curve values $U_A$ are to be determined, and the point in time of causing the voltage reading, in relation to which the multitude of compensating-curve values $U_A$ are to be determined;

in relation to a multitude of combinations of a value of the first parameter $U_0$ and/or a value of the second parameter $\tau$ to determine the sum of the squares of the differences of all voltage values measured during the more than two current pulses, and of the compensating-curve value $U_A$ calculated in relation to each voltage value according to the respective combination of a value of the first parameter $U_0$ and/or of a value of the second parameter $\tau$;

as well as by selecting the lowest sum to issue a combination of a value of the first parameter $U_0$ and/or of a value of the second parameter $\tau$ and to issue it as a result parameter combination.

4. The electromedical implant according to claim 2, wherein:

the control unit is programmed at more than two different points in time to cause the measuring signal generator to generate and emit a current pulse so that emission of the first current pulse ends before commencement of emission of the second current pulse, and so that the pulse durations of the emitted current pulses differ from each other;

and to cause the impedance measuring unit to measure the voltage that is present between the electrodes that are connected to the measuring signal generator and the impedance measuring unit by measuring a first voltage at the beginning of a specific period of time which ends when emission of the first current pulse ends; and by measuring a second voltage at the beginning of said specific period of time that ends when emission of the second current pulse ends;

and wherein furthermore, the control unit is programmed to determine the coefficients of a polynomial which acts as a compensating curve, in relation to which polynomial the sum of the squares of the differences of all voltage values measured during the more than two current pulses and the values of the function of the polynomial for the points in time of causing a voltage reading from the point in time of the beginning of emission of the respective current pulse is minimal, and to issue them as a result coefficient.

5. The electromedical implant according to claim 4, wherein:

the measuring signal generator is adapted to generate current pulses of variable pulse duration, wherein the pulse duration is at least a first duration and at the longest a second duration;

and wherein the control unit is programmed to cause the measuring signal generator to emit a larger number of current pulses of comparatively short pulse duration than of current pulses of comparatively longer pulse duration.

6. The electromedical implant according to claim 5, wherein:

the control unit is programmed to determine a value that represents a difference between the compensating-curve values $U_A$ of the result parameter combination or of the result coefficients in relation to the durations t of the current pulses with the longest and shortest pulse durations and to issue said value as a voltage difference value.

7. The electromedical implant according to claim 6, wherein:

the measuring signal generator is adapted to generate biphasal current pulses.

8. The electromedical implant according to claim 7, wherein:

the impedance measuring unit is programmed to take impedance readings during emission of differently polarised segments of a biphasal current pulse through the measuring signal generator;

and wherein the control unit is programmed to relate the values obtained in this way and to determine and issue a differential value obtained, which value represents a difference between two values obtained during emission of differently polarised segments of a biphasal current pulse.

9. The electromedical implant according to claim 1, wherein:

the electromedical implant comprises more than two electrodes or can be connected to more than two electrodes;

and wherein the impedance measuring unit is adapted to be connected to a selectable electrode and to a fixed or selectable electrode, and to measure a voltage that is present between these electrodes.

10. The electromedical implant according to claim 9, wherein:

the electromedical implant comprises more than two electrodes or can be connected to more than two electrodes;

and wherein the measuring signal generator is adapted to be connected to a selectable electrode and a fixed or selectable electrode.

11. The electromedical implant according to claim 10, wherein:

the control unit is programmed in relation to several different combinations of two electrodes that are connected or adapted to be connected with the impedance measuring unit and the measuring signal generator to emit a current pulse or a sinusoidal current, and to cause the impedance measuring unit to measure the voltage that is present between the respective combination of two electrodes and to calculate and issue an average value of the voltage values that have been determined in this way and that represent the measured voltages.

12. The electromedical implant according to claim 11, wherein:

the electromedical implant is a cardiac pacemaker, cardioverter or defibrillator.

13. The electromedical implant according to claim 12, wherein:

the electromedical implant comprises a cardiac activity detector which is designed to register the cardiac cycle of a patient and at a defined point in time within a cardiac cycle, to issue a signal to the control unit;

and wherein the control unit is programmed, after receiving a signal from the cardiac activity detector, to cause the measuring signal generator to generate a current pulse or a measuring signal and to emit said current pulse or measuring signal by way of at least one electrode.

14. The electromedical implant according to claim 13, wherein:

the electromedical implant comprises a respiratory activity detector which is designed to register the respiratory cycle of a patient and at a defined point in time within a respiratory cycle to issue a signal to the control unit;

and wherein the control unit is programmed, after receiving a signal from the cardiac activity detector, to cause the measuring signal generator to generate a current pulse or a measuring signal and to emit said current pulse or measuring signal by way of at least one electrode.

15. The electromedical implant according to claim 14, wherein:
the electromedical implant is programmed to take series of impedance readings;
and wherein the control unit is programmed to determine the average value of the readings obtained in a series of impedance readings and to issue it as a resulting value.

16. The electromedical implant according to claim 15, wherein:
the electromedical implant is programmed to take series of impedance readings;
and wherein the control unit is programmed to determine the median of the readings obtained in a series of impedance readings and to issue it as a resulting value.

17. The electromedical implant according to claim 16, wherein:
the electromedical implant comprises a wireless data transmission interface;
and wherein the wireless data transmission interface is programmed to transmit to a home monitoring service center one or several of the parameters, determined or issued by the control unit, such as the voltage difference value, average value, value of the first parameter $U_0$, value of the second parameter $\tau$ and amplitude difference value and/or one or several of the voltage values or amplitude values determined by the impedance measuring unit, by way of the wireless data transmission interface directly or indirectly as patient data.

18. A system comprising at least
an electromedical implant according to claim 17
and at least one of a patient device and a home monitoring service center;
wherein the electromedical implant and the patient device can be connected to each other by way of wireless data transmission interfaces, and the patient device and the home monitoring service center can be connected to each other by way of a wireless or a wire-bound data transmission interface.

19. The system according to claim 18, wherein:
the patient device or the home monitoring service center is programmed to store the patient data received by the electromedical implant and to calculate short-term and long-term average values of individual patient data.

20. The system according to claim 19, wherein:
the patient device or the home monitoring service centre are programmed to compare received patient data with the calculated short-term and long-term average values.

21. The system according to claim 20, wherein:
the patient device or the home monitoring service centre are programmed to display any deviations between the short-term and long-term average values and the patient data compared with the short-term and long-term average values.

* * * * *